(12) United States Patent
Petinarides

(10) Patent No.: US 7,963,146 B2
(45) Date of Patent: Jun. 21, 2011

(54) METHOD AND SYSTEM FOR DETECTING VAPORS

(75) Inventor: John M. A. Petinarides, Waxhaw, NC (US)

(73) Assignee: General Dynamics Armament and Technical Products, Inc., Charlotte, NC (US)

( * ) Notice: Subject to any disclaimer, the term of this patent is extended or adjusted under 35 U.S.C. 154(b) by 529 days.

(21) Appl. No.: 11/748,258

(22) Filed: May 14, 2007

(65) Prior Publication Data

US 2008/0282772 A1 Nov. 20, 2008

(51) Int. Cl.
*G01N 7/00* (2006.01)
(52) U.S. Cl. .................. 73/31.02; 73/31.07; 73/863.23; 73/864.81
(58) Field of Classification Search ............. 73/31.01, 73/31.02, 31.07, 863.21, 863.23, 864.81
See application file for complete search history.

(56) References Cited

U.S. PATENT DOCUMENTS

| | | | |
|---|---|---|---|
| 3,976,450 A * | 8/1976 | Marcote et al. ............. 96/12 |
| 4,019,863 A * | 4/1977 | Jenkins et al. ............. 250/304 |
| 4,906,257 A | 3/1990 | Fukunaga et al. |
| 5,639,956 A * | 6/1997 | Christy ..................... 73/19.01 |
| 5,723,861 A | 3/1998 | Carnahan et al. |
| 6,418,965 B2 | 7/2002 | Bryselbout |
| 6,495,823 B1 | 12/2002 | Miller et al. |
| 6,512,224 B1 | 1/2003 | Miller et al. |
| 6,690,004 B2 | 2/2004 | Miller et al. |
| 6,727,496 B2 | 4/2004 | Miller et al. |
| 6,806,463 B2 | 10/2004 | Miller et al. |
| 6,809,313 B1 | 10/2004 | Gresham et al. |
| 6,815,668 B2 | 11/2004 | Miller et al. |
| 6,815,669 B1 | 11/2004 | Miller et al. |
| 6,948,929 B2 | 9/2005 | Komai et al. |
| 6,972,407 B2 | 12/2005 | Miller et al. |
| 7,005,632 B2 | 2/2006 | Miller et al. |
| 7,030,372 B2 | 4/2006 | Miller et al. |
| 7,318,858 B2 * | 1/2008 | Parsa ..................... 96/60 |

(Continued)

FOREIGN PATENT DOCUMENTS

DE 102005018142 10/2006

(Continued)

OTHER PUBLICATIONS

"Differential Mobility Spectrometry: The Technology Of Choice For Miniaturized, High Performance, Fieldable Chemical And Biological Detection Systems", ECE 500: ECE Seminar—Raanan Miller, Graduate Seminar, http://www.ece.uiuc.edu/seminar/05-06/dec01-05-miller.html, Dec. 1, 2005, (2 pages).

(Continued)

Primary Examiner — Daniel S Larkin
(74) Attorney, Agent, or Firm — Hunton & Williams

(57) ABSTRACT

A method and system may include receiving a sample gas from an ambient environment on a first surface of a selective isolation device within an inlet assembly, dispersing the sample gas in substantially a first direction along the first surface, and circulating a carrier gas through a main assembly coupled to the inlet assembly, the main assembly defining a carrier gas environment. The method and system also may include selectively passing analytes from the sample gas through the selective isolation device to a second surface of the selective isolation device, the selective isolation device separating the ambient environment from the carrier gas environment, dispersing the carrier gas in substantially a second direction along the second surface, and obtaining the analytes in the carrier gas from the second surface.

22 Claims, 9 Drawing Sheets

U.S. PATENT DOCUMENTS

| | | |
|---|---|---|
| 2001/0049998 A1 | 12/2001 | Rode et al. |
| 2002/0139245 A1 | 10/2002 | Kesten et al. |
| 2005/0092914 A1 | 5/2005 | Miller et al. |
| 2005/0156107 A1 | 7/2005 | Miller et al. |
| 2006/0100744 A1 | 5/2006 | Sharma et al. |
| 2007/0228269 A1 | 10/2007 | Miller et al. |
| 2008/0066619 A1 | 3/2008 | Petinarides |

FOREIGN PATENT DOCUMENTS

| | | |
|---|---|---|
| WO | WO 2006/110700 | 10/2006 |

OTHER PUBLICATIONS

GB0708425.4 UK Search Report dated Aug. 28, 2007.

Notification of Transmittal of the International Search Report and the Written Opinion of the International Searching Authority, or the Declaration, dated Feb. 25, 2009.

Notification of Transmittal of the International Search Report and the Written Opinion of the International Searching Authority, or the Declaration, dated Mar. 6, 2009.

Notification of Transmittal of the International Search Report and the Written Opinion of the International Searching Authority, or the Declaration, dated Feb. 20, 2009.

Yang, Ralph T., "Absorbents: Fundamentals and Applications," Wiley Online Library http//onlinelibrary.wiley.com/book/10.1002/047144409X Jun. 2003 (1 page).

Knaebel, K.S., "Adsorbent Selection," Adsorption Research Inc., http//www.adsorption.com/publications.AdsorbentSel1B.pdf, Jun. 2004 (24 pages).

* cited by examiner

METHOD AND SYSTEM FOR DETECTING VAPORS

FIELD OF THE INVENTION

The present invention relates to detection, and more specifically to chemical detection.

BACKGROUND OF THE INVENTION

Detection of chemicals is increasingly important. Warfare, terrorism, catastrophes, and other such events may potentially expose people to harmful chemicals. Techniques using mass spectrometry, time-of-flight Ion Mobility Spectrometry (IMS), differential mobility spectrometry (DMS), and field asymmetric ion mobility spectrometry (FAIMS) are known for detecting chemicals. One known system for detecting chemicals is described in U.S. Pat. No. 7,005,632 to Miller et al. titled "Method and Apparatus for Control of Mobility-based Ion Species Identification," the contents of which are hereby incorporated by reference in their entirety.

SUMMARY OF THE INVENTION

An apparatus according to exemplary embodiments may include a gas permeable selective isolation device including a first surface and a second surface, an inlet assembly to receive sample gas from an ambient environment and to substantially disperse the sample gas along the first surface of the selective isolation device in a first direction, and a main assembly defining a carrier gas environment for circulating a carrier gas, the main assembly comprising a carrier inlet to receive the carrier gas, the main assembly for substantially dispersing the carrier gas along the second surface of the selective isolation device in a second direction differing from the first direction, wherein the selective isolation device separates the ambient air environment from the carrier gas environment and selectively passes analytes in the sample gas therethrough.

An apparatus according to other exemplary embodiments may include an inlet assembly comprising a gas permeable selective isolation device, the inlet assembly for receiving sample gas from an ambient environment and for substantially dispersing the sample gas along a first surface of the selective isolation device in a first direction, and a main assembly coupled to the inlet assembly and comprising a carrier inlet to receive a carrier gas, the main assembly defining a carrier gas environment and substantially dispersing the carrier gas along a second surface of the selective isolation device in a second direction, wherein the selective isolation device separates the ambient environment from the carrier gas environment and selectively passes analytes in the sample gas through the selective isolation device from the first surface to the second surface.

A system according to exemplary embodiments may include a sampling pump for circulating a sample gas from an ambient environment, a gas distribution system for circulating a carrier gas, and a vapor detector coupled to the sampling pump and to the gas distribution system, the vapor detector may include a main assembly comprising a carrier inlet to receive the carrier gas from the gas distribution system, the main assembly defining a carrier gas environment for circulating the carrier gas, and an inlet assembly coupled to the main assembly and to the sampling pump, the inlet assembly comprising a gas permeable selective isolation device, the inlet assembly for receiving the sample gas from the ambient environment by a vacuum created by the sampling pump, the selective isolation device for separating the ambient environment from the carrier gas environment and for selectively passing analytes in the sample gas therethrough.

A method according to exemplary embodiments may include receiving a sample gas from an ambient environment on a first surface of a selective isolation device within an inlet assembly, dispersing the sample gas in substantially a first direction along the first surface, circulating a carrier gas through a main assembly coupled to the inlet assembly, the main assembly defining a carrier gas environment, selectively passing analytes from the sample gas through the selective isolation device to a second surface of the selective isolation device, the selective isolation device separating the ambient environment from the carrier gas environment, dispersing the carrier gas in substantially a second direction along the second surface, and obtaining the analytes in the carrier gas from the second surface.

BRIEF DESCRIPTION OF THE FIGURES

The accompanying drawings, which are incorporated in and constitute a part of this specification, illustrate embodiments of the invention and, together with the description, serve to explain the principles of the invention.

In the drawings.

DESCRIPTION OF THE PREFERRED EMBODIMENTS

The following description is intended to convey a thorough understanding of the invention by providing a number of specific embodiments and details involving a system and method for detecting vapors. It is understood, however, that the invention is not limited to these specific embodiments and details, which are exemplary only. It is further understood that one possessing ordinary skill in the art, in light of known systems and methods, would appreciate the use of the invention for its intended purposes and benefits in any number of alternative embodiments.

Figure 1:
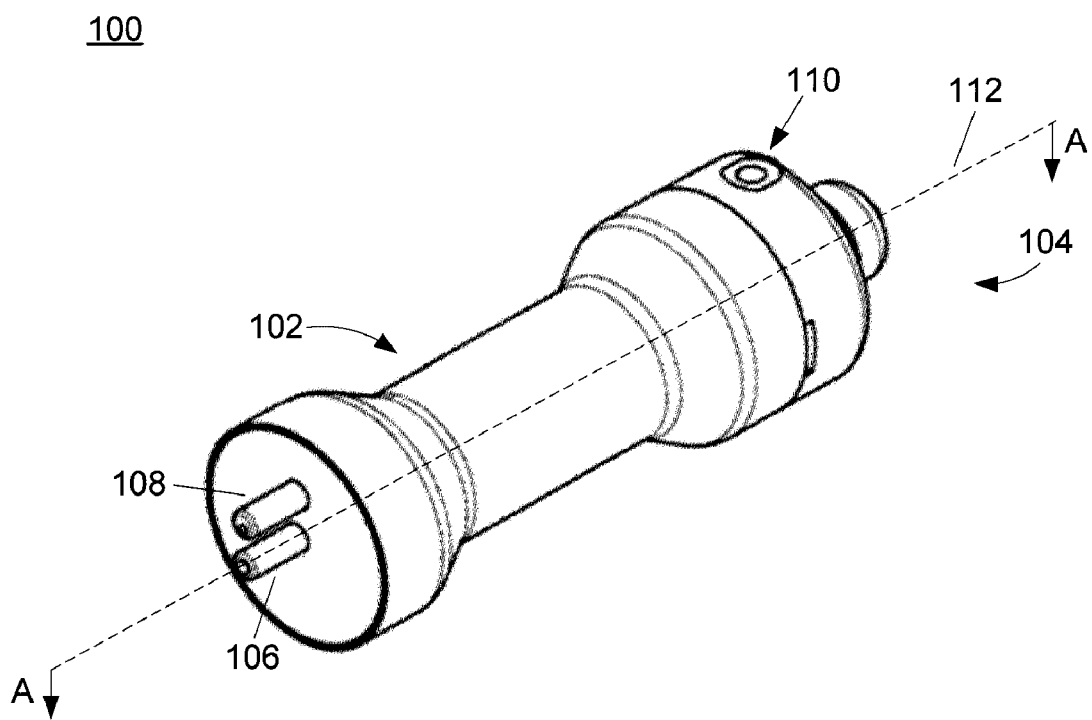
FIG. 1 illustrates an exemplary embodiment of a vapor detector.

FIG. 1 illustrates an exemplary embodiment of a vapor detector 100, which may be used for chemical analysis of chemicals contained within a sample gas sampled from an ambient air environment. A perspective view of the vapor detector 100 is depicted with a longitudinal axis 112. The vapor detector 100 may ionize the sample gas at various pressures to identify chemicals within the sample gas. The vapor detector 100 may identify chemicals within the sample gas due to ions of different chemical species having different ion mobility characteristics under different electric field conditions at elevated pressure conditions, which may include atmospheric pressure, and/or reduced pressure conditions. In an exemplary embodiment, the vapor detector 100 may be a differential mobility spectrometer (DMS) detector, a field asymmetric ion mobility spectrometry (FAIMS) detector, a field ion spectrometry (FIS) detector, and/or combinations thereof. Description of chemical analysis using the vapor detector 100 is further described in detail below.

The vapor detector 100 may detect various chemical species within gas sampled from an ambient air environment. The ambient air environment may be air inside or outside of a building, for example. The chemicals may include, for example, chemical warfare agents, nerve agents, blister agents, choking agents, toxic industrial chemicals (TICs), toxic industrial materials (TIMs), low vapor compounds, explosives, narcotics, etc., and/or combinations thereof. The vapor detector 100 also may detect organic chemicals, hydrocarbons, and/or combinations thereof. The vapor detector 100 may be used in various applications and may be designed to meet the detector requirements of various jurisdictions, such as the requirements of the United States government and the Canadian Government, for example.

Figure 2:
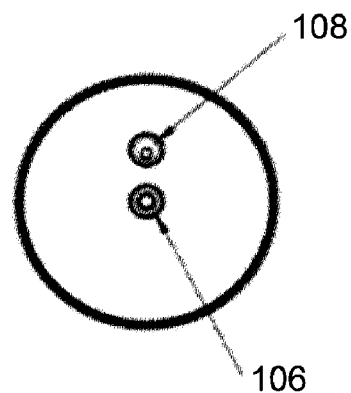
FIG. 2 illustrates an end view of an exemplary vapor detector.
Figure 3:
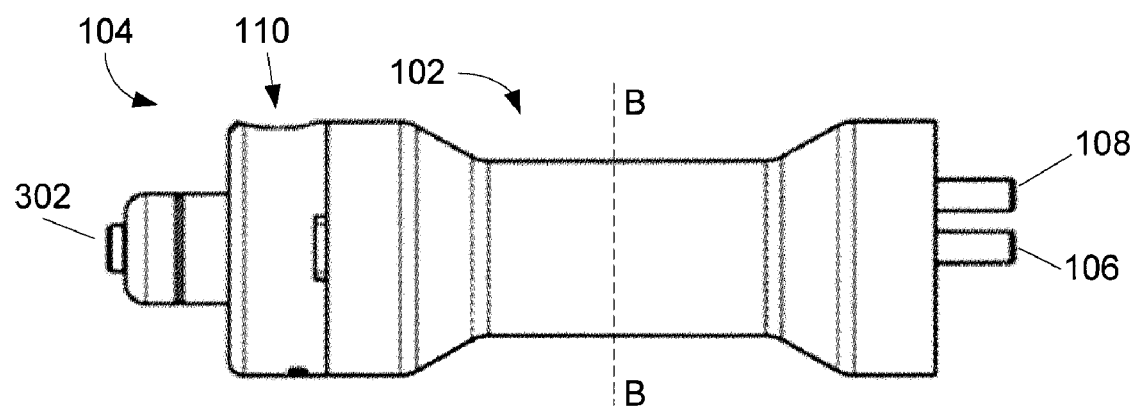
FIG. 3 illustrates a side view of an exemplary vapor detector.

The vapor detector 100 includes a housing 102 coupled to an inlet assembly 104. The shape of the housing 102 may be cylindrical to provide a compact coaxial carrier gas arrangement and analytical filter region for the measurement of vapors. FIG. 2 depicts a first end of the housing 102. The first end of the housing 102 includes carrier input 106 and carrier outlet 108. Carrier input 106 may receive a carrier gas for input into the vapor detector 100 and extends through the vapor detector 100 to the inlet assembly 104. A carrier output 108 is coupled to the carrier input 106 and exhausts carrier gas from the vapor detector 100 to atmosphere or to a gas distribution system for recirculation through the vapor detector 100. FIG. 3 depicts a side view of the housing 102 of the vapor detector 100. The inlet assembly 104 is attached to a second end of the housing 102. The inlet assembly 104 receives ambient air through inlet 302, and outputs the ambient air at outlet 110.

Figure 4:
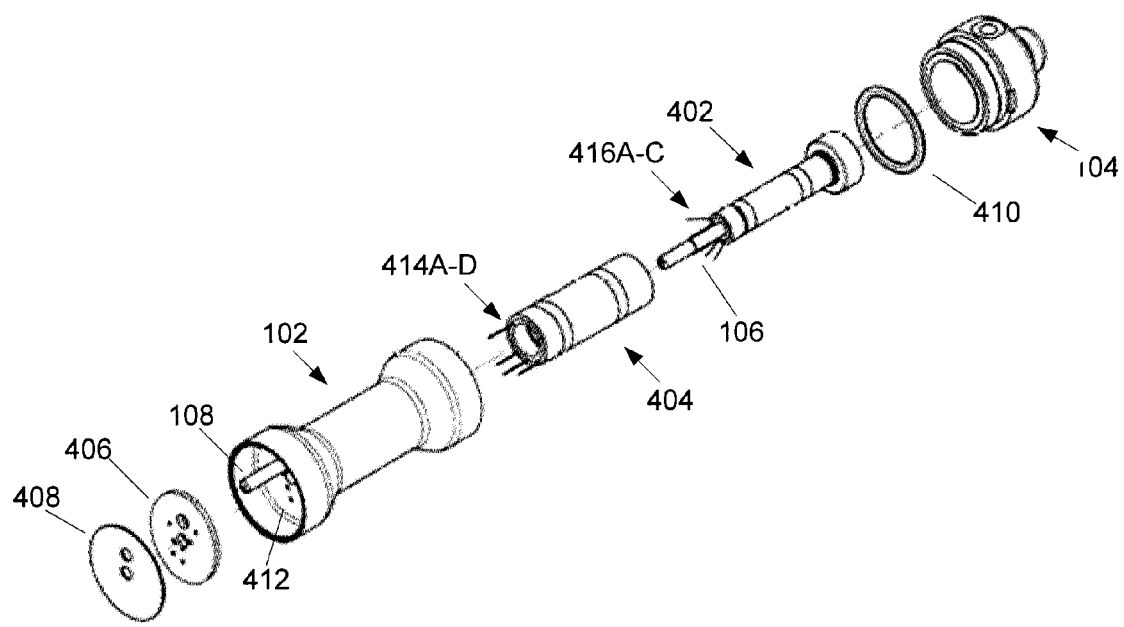
FIG. 4 illustrates an exploded view of an exemplary vapor detector.

FIG. 4 illustrates an exploded view of the vapor detector 100. The vapor detector 100 may include the inlet assembly 104, a main assembly comprising an inner assembly 402 and an outer assembly 404, the housing 102, an amplifier 406, a casing 408, and a sealing ring 410. During manufacturing, the inner assembly 402 may be inserted into a cylindrical opening that longitudinally extends through the outer assembly 404. The outer assembly 404 may then be inserted into a cylindrical opening that longitudinally extends through the housing 102 to abut against a wall 412 within the housing 102. Electrical leads 414A-D on the outer assembly 404 and electrical leads 416A-C on the inner assembly 402 of the carrier inlet 106 may be inserted through the wall 412. The amplifier 406 may be positioned on the other side of the wall 412 within the housing 102 and may be electrically coupled to the electrical leads 414A-D and to electrical leads 416A-C. The casing 408 may be inserted into the housing 102 after the amplifier 406 to maintain and protect the amplifier 406 within the housing 102.

The inlet assembly 104 may be coupled to the housing 102 via the sealing ring 410. In an exemplary embodiment, the sealing ring 410 may create an air tight seal between the housing 102 and the inlet assembly 104 to prevent the ambient sample gas from escaping at the interface between the inlet assembly 104 and the housing 102. For example, the sealing ring 410 may be an O-ring.

Figure 5:
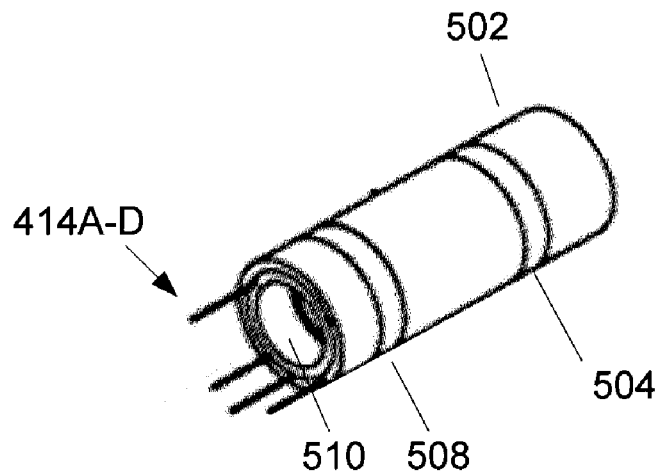
FIG. 5 illustrates a perspective view of an exemplary outer assembly of an exemplary vapor detector.
Figure 7:
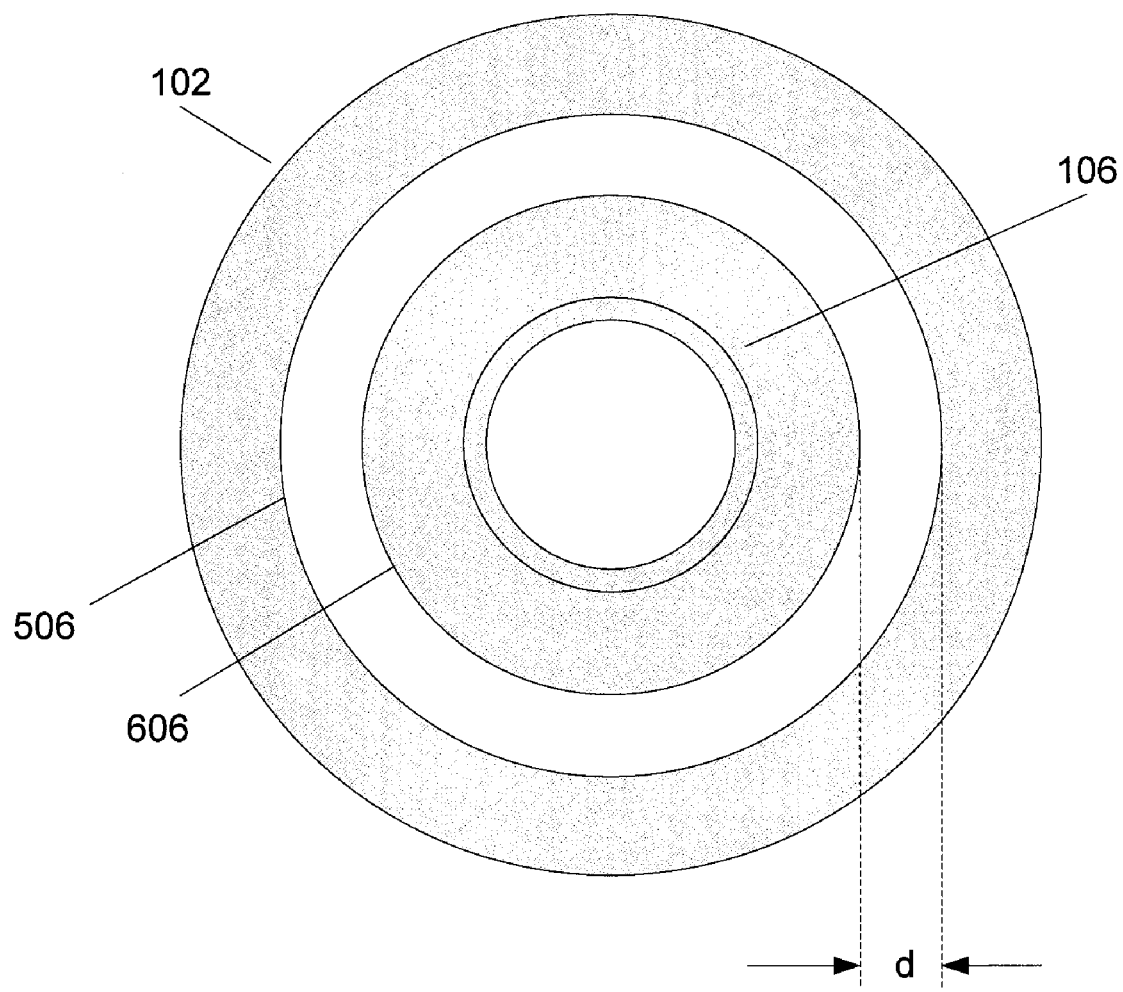
FIG. 7 illustrates a cross-sectional view of an exemplary vapor detector along a vertical axis of an exemplary vapor detector.

FIG. 5 further depicts an exemplary embodiment of the outer assembly 404. The outer assembly 404 may have a substantially cylindrical shape and may include an outer ionization source 502, a first outer insulator 504, a second outer insulator 508, and an outer collector electrode 510. The outer assembly 404 also includes an outer electrode 506 positioned on an interior surface, which is depicted in FIGS. 7 and 8. The outer assembly 404 may be composed of a non-conductive material, except for at the outer electrode 506, at the outer collector electrode 510, and at the ionization source 502. For example, the outer assembly 404 may be composed of plastic. Each of the outer electrode 506 and the outer collector electrode 510 may be a separate cylinder composed of electrically conductive material (e.g., metal) positioned on the inner surface of the plastic within the cylindrical opening through the outer assembly 404. The first outer insulator 504 may substantially electrically insulate the ionization source 502 from the outer electrode 506. The second outer insulator 508 may substantially electrically insulate the outer electrode 506 from the outer collector electrode 510.

Figure 6:
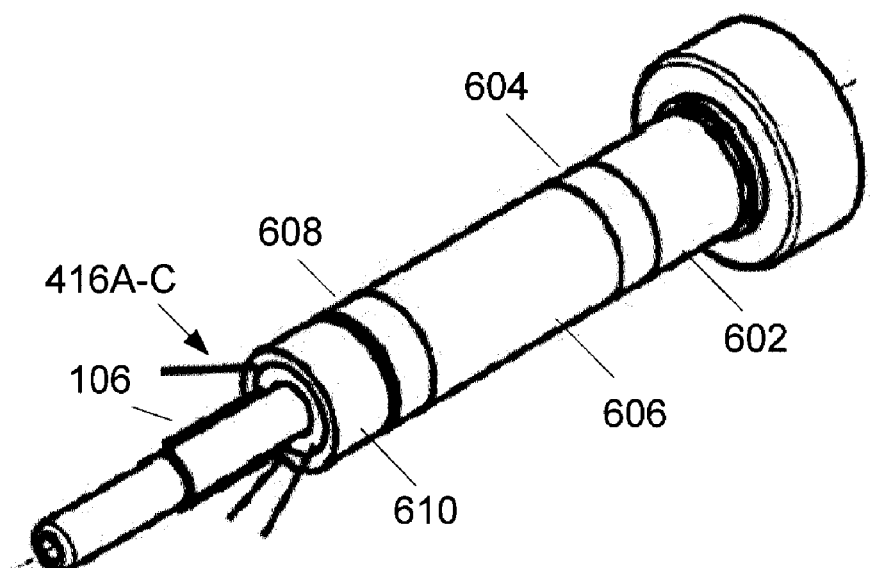
FIG. 6 illustrates a perspective view of an exemplary inner assembly of an exemplary vapor detector.

FIG. 6 further depicts the inner assembly 402. The inner assembly 402 may have a substantially cylindrical shape and may include the carrier inlet 106, an inner ionization source 602, a first inner insulator 604, an inner electrode 606, a second inner insulator 608, and an inner collector electrode 610. The carrier inlet 106 may define a substantially cylindrical gap extending through the inner assembly 402. The inner assembly 402 may be composed of a non-conductive material, except for at the ionization source 602, at the inner electrode 606, and at the inner collector electrode 610. For example, the inner assembly 402 may be composed of plastic. Each of the inner electrode 606 and the inner collector electrode 610 may be a separate cylinder composed of an electrically conductive material (e.g., metal) positioned on the outer surface of the plastic of the inner assembly 402. The first inner insulator 604 may substantially electrically insulate the ionization source 602 from the inner electrode 606. The second inner insulator 608 may substantially electrically insulate the inner electrode 606 from the outer collector electrode 610.

During assembly of the vapor detector 100, the inner assembly 402 may be positioned within the outer assembly 404. FIG. 7 illustrates a cross-sectional view of the inner assembly 402 positioned within the outer assembly 404 along line B-B of FIG. 3. Line B-B cuts through housing 102, the outer electrode 506, the inner electrode 606, and the carrier inlet 106. The ionization sources 502 and 602 and the collector electrodes 510 and 610 have similar cross-sections as the one depicted in FIG. 7. It is noted that the vapor detector 100 may only include a single ionization source (e.g., ionization source 502 or 602) or may include both ionization sources.

FIG. 7 illustrates a gap of a distance 'd' between the inner electrode 606 and the outer electrode 506. The gap may be a cylindrical space in between the inner electrode 606 and the outer electrode 506 permitting the carrier gas to flow though the vapor detector 100. The gap between the inner assembly 402 and the outer assembly 404 may be referred to as an analytical gap. The vapor detector 100 may process the analytes within the carrier gas passing through the analytical gap.

Figure 8A:
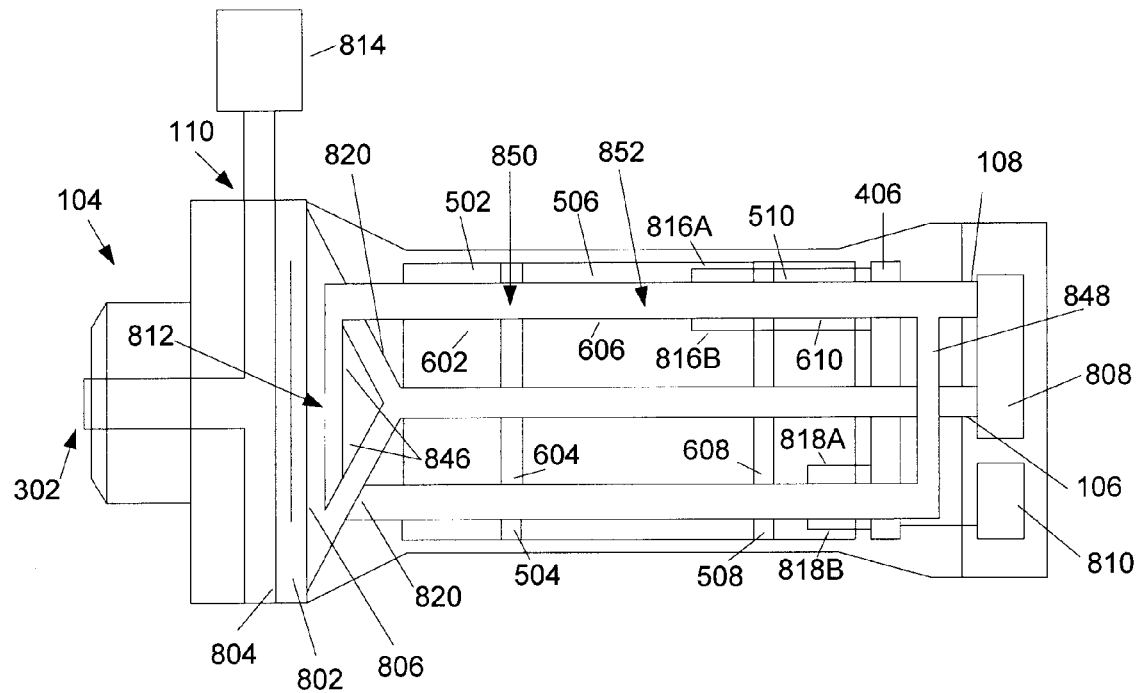
FIGS. 8A-B illustrate cross-sectional views along a longitudinal axis of an exemplary vapor detector.
Figure 8B:
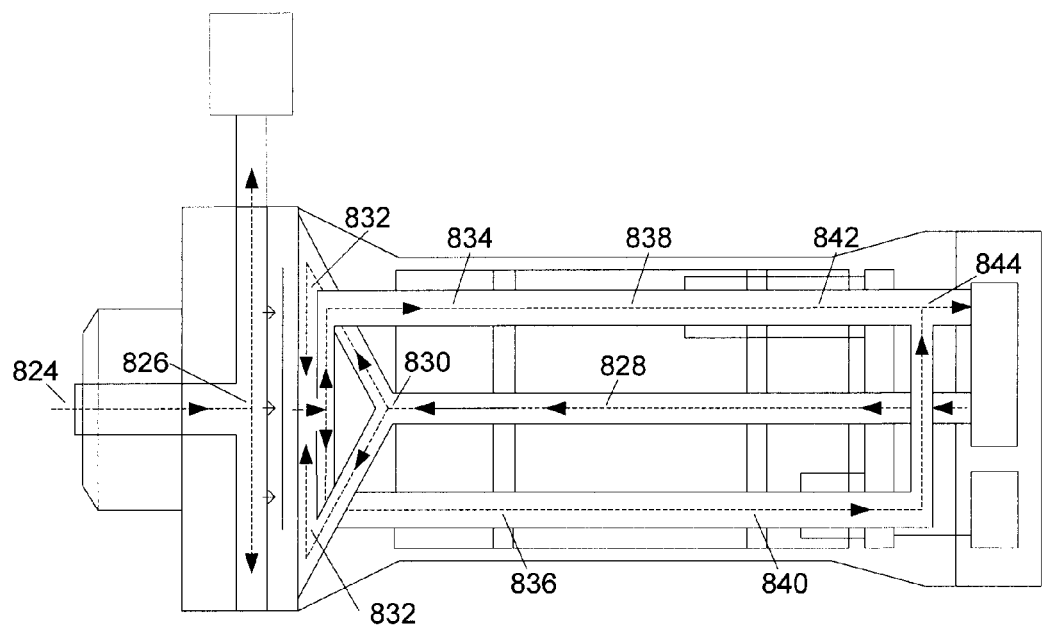

FIGS. 8A-B illustrate longitudinal cross-sectional views of the vapor detector 100, with FIG. 8A illustrating reference characters for the components and with FIG. 8B illustrating reference characters to show flow of the sample gas and of the carrier gas through the vapor detector 100. A sampling pump 814 may be coupled to the outlet 110 to create a vacuum for drawing a sample gas from an ambient air environment into the inlet assembly 104 at the inlet 302 (see FIG. 8B, flow path 824). The inlet assembly 104 may include a heating element or other heating device (not shown) to facilitate flow of the sample gas through the inlet assembly 104. The heating element may prevent chemical species within the sample gas from adhering to a wall of the inlet assembly 104, for example. Also, the inlet assembly 104 may not include the heating element and may vary a diameter and/or length of the inlet 302 to facilitate flow of the sample gas therethrough. At path 826, the sample gas may contact a surface 804 of membrane 802 (or some other form of a selective isolation device or sample flow control device, such as, for example, a valve or an orifice) within the inlet assembly 104. This contact may cause the sample gas to disperse substantially radially along the surface 824 relative to the longitudinal axis of the vapor detector 100. The sample gas may contact the surface 824 near the longitudinal axis of the vapor detector 100 and may disperse radially outward toward the cylindrical outer surface of the inlet assembly 104. The sampling pump 814 may then draw the sample gas out of the inlet assembly 104 and exhaust the sample gas. The sampling pump 814 may draw the sample gas intermittently or continuously into the inlet assembly 104 from the ambient environment.

Integration of the membrane 802 into the inlet assembly 104 may permit for efficient transfer of the sample gas into the membrane 802 or other sample flow control mechanism, thus permitting the vapor detector 100 to quickly identify the presence of a hazardous vapor and to generate an alarm.

The membrane 802 may be gas-permeable and may permit molecules of the sample gas to pass through the first surface 804 into the membrane 802. Contact with the sample gas may cause the membrane 802 to absorb some of the sample gas and may pass the absorbed gas through the membrane 802. The membrane 802 also may selectively block certain molecules from passing. For example, the membrane 802 may permit certain chemical species and/or chemical classes to pass therethrough and substantially inhibit other chemical species and/or chemical classes from passing therethrough. Membranes of different materials and thicknesses and surface area, held at various temperatures, either uniform or gradient can be used based on their permeation characteristics and operating temperature to allow molecules of interest to pass, over those that may interfere with the detection process. A specific membrane or sample control mechanism may be selected for particular detection applications.

The membrane 802 also may keep the carrier gas in the carrier gas environment separate from the sample gas obtained from the ambient air environment, except for molecules of the sample gas permitted to pass through the membrane 802. The separation performed by the membrane 802 may prevent contaminants from the ambient environment being introduced into the carrier gas environment and also may be used to maintain the carrier gas at a desired moisture level within the vapor detector 100. This separation advantageously maintains the integrity of the carrier gas and improves the ability of the vapor detector 100 to accurately identify chemicals within the sample gas.

The molecules of the sample gas passing through the membrane 802 may be referred to analytes. The analytes may accumulate on the second surface 806 of the membrane 802 and may be removed by the carrier gas.

A gas distribution system 808 may be coupled to the housing 102 for continuously or intermittently circulating the carrier gas through of the vapor detector 100. The main assembly including the inner assembly 402 and the outer assembly 404 within the housing 102 may define a carrier gas environment of the vapor detector 100 through which the carrier gas may circulate. The carrier gas environment is a self-contained flow path through the vapor detector 100 that may not interact with the ambient environment except for any analytes that pass through the membrane 802. The gas distribution system 808 also may maintain the carrier gas circulating within the carrier gas environment at a desired moisture level. Water molecules at higher concentrations may cluster with molecules of interest (analytes) and diminish the ability of the vapor detector 100 to identify the analytes. The range of acceptable moisture depends on the analytes required to be detected, and the desired moisture level of the carrier gas within the vapor detector 100 may be modified accordingly.

The gas distribution system 808 may be coupled to the carrier inlet 106 and to the carrier outlet 108. The carrier gas may be clean air or another gas better suited to the ion chemistry of the analyte of interest. The carrier gas also may include dopants, which may be used manipulate the charge affinity of ions. For example, the carrier gas may include dopants such as acetone or ammonia. Dopants may be used to improve the resolution of the vapor detector 100 for distinguishing between different chemical species by modifying the affinity of the ions in an electric field.

In an exemplary embodiment, the gas distribution system 808 is a carrier gas source which may be part of a pump driven recirculating system that recirculates carrier gas through the vapor detector 100. The gas distribution system 808 may include air purifiers, scrubbers, or other devices for purifying the carrier gas circulating in the carrier gas environment. Also, the gas distribution system 808 may provide a continuous supply of carrier gas to the carrier inlet 106 and may release carrier gas to atmosphere at the carrier outlet 108 that has previously passed through the vapor detector 100. The continuous supply of carrier gas may be supplied by a tank of carrier gas coupled to the gas distribution system 808.

The carrier inlet 106 may transport the carrier gas from the gas distribution system 808 through the housing 102 toward the membrane 802 (see FIG. 8B, path 828). Prior to reaching the membrane 802, a series of radially spaced angled shafts 820 split the gas path (see FIG. 8B, paths 830) and direct the carrier gas toward the outer radius of the second surface 806 of the membrane 802. From the outer radius, the carrier gas may flow substantially radially inward toward the longitudinal axis 112 of the vapor detector 100 (also see FIG. 1) against the second surface 806 of the membrane 802 (see FIG. 8B, paths 832). The contact of the carrier gas with the second surface 806 may cause the carrier gas to obtain analytes that have permeated through the membrane 802.

From the second surface 806, the carrier gas is then drawn into a central hole 812. A series of radial shafts 846, which are radially offset from the radially spaced angled shafts 820, lead radially outward from the central hole 812 and direct the carrier gas outward from the longitudinal axis of the housing 102 toward a cylindrical analytical gap between the ionization sources 502 and 602 (see FIG. 8B, path 834). The cylindrical analytical gap is the open cylindrical region between the inner assembly 402 and the outer assembly 404 that extends from the radial shafts 846 to an annular gap 848 after the amplifier 406.

The ionization sources 502 and 602 may ionize the analytes (see FIG. 8B, path 834), which react in an ion reaction region 850. The ion reaction region 850 substantially occurs between the insulators 504 and 604 before the carrier gas and analytes reach the electrodes 506 and 606. The ionization sources 502 and 602 may be a Nickel 63 (Ni63) source, a corona, a plasma, or other known sources for ionizing chemicals, as are well known. Also, the ionization sources 502 and 602 may be plasma generators for ionizing the analytes. Other radioactive materials, such as, for example, Americium also may be used for ionizing the analytes. The type of ionizing source may be selected based on the preferred ion affinity of the analytes, and power and life required from the ionizing source.

The ion reaction region 850 may be optimized by changing a radial distance between the insulator 604 and the insulator 504. The ion reaction region 850 also may be optimized by changing a longitudinal distance of the insulator 604 and the insulator 504 along the longitudinal axis of the vapor detector 100. Both the radial distance and the longitudinal distance also may be varied. Changing the radial distance and/or the longitudinal distance may affect the resolution of the vapor detector 100, as will be discussed below in further detail. After ionization of the analytes and passing through the ion reaction region 850, the carrier gas may transport the ionized analytes into an analyzer (see FIG. 8B, path 838).

The analyzer may include the outer electrode 506 and the inner electrode 606 for generating an electric field therebetween. The electrodes 506 and 606 are two metalized cylinders coaxially contained within the housing 102 such that an uniform radial distance is maintained between the electrodes 506 and 606. The outer electrode 506 may include an outer conductive cylinder and the inner electrode 606 may include an inner conductive cylinder, where the outer conductive cylinder and the inner conductive cylinder are concentric. The carrier gas may pass through the cylindrical opening between the outer conductive cylinder and the inner conductive cylinder.

A signal generator and signal processor (SGSP) 810 may identify ion species by ion mobility behavior in an electric field between the electrodes 506 and 606. Known signal generators and signal processors may be used. The SGSP 810 detects differences in an ionized analytes' mobility between high and low electric field conditions and classifies the ionized analytes according to these differences. These differences reflect ion properties such as charge, size, and mass, as well as the collision frequency and energy obtained by ions between collisions. These differences may be used to identify the ionized analytes by chemical species.

The SGSP 810 may be coupled to the electrodes 506 and 606 by wires 816A-B through the amplifier 406. The wires 816A-B may be positioned within the non-conductive material of the inner assembly 402 and the outer assembly 404 surrounding the electrodes 506 and 606. The SGSP 810 may generate an electric field between the electrodes 506 and 606 transverse to the carrier gas flow in the analytical gap. The electric field between the outer electrode 506 and the inner electrode 606 filters ion analytes based on various characteristics of the ions. The electric field may be an asymmetric radio frequency (RF) field, which also may be referred to as a filter field, a dispersion field, or a separation field. Field strength of the electric field may vary based on the applied asymmetric RF voltage (sometimes referred to as dispersion or separation voltage) and on the radial distance between the electrodes 506 and 606.

The SGSP 810 uses various AC and DC voltages and frequencies to filter the ionized analytes within the carrier gas passing between the electrodes 506 and 606. The signal generator 810 may generate the electric field that biases ionized analytes of interest along a central path between the outer electrode 506 and the inner electrode 606. The electric field transversely displaces ions between the electrodes 506 and 606, with each chemical species being displaced a distance toward the electrodes 506 and 606 per cycle of the electric field. Due to ions having different size and mass, the electric field may cause the ions not of interest to be attracted to either the outer electrode 506 or the inner electrode 606, which neutralizes and removes the ions not of interest from the carrier gas.

To form the electric field, the SGSP 810 may generate an electrical waveform that passes through the amplifier 406 and onto the outer electrode 506 and the inner electrode 606. The SGSP 810 may be battery operated and/or may include a cord for connection to an external power source, for example. The electrical waveform may be a asymmetric radio frequency (RF) alternating current (AC) voltage, for example. The electrical waveform also may include a direct current (DC) voltage, which may be referred to as a compensation voltage. The compensation voltage reduces the alternating attraction to the outer electrode 506 and the inner electrode 606 caused by the asymmetric RF AC voltage to maintain ionized analytes of interest on a central path between the electrodes 506 and 606. The amount of compensation voltage depends upon characteristics of the chemical species, and may be used to identify the presence or absence of a particular chemical species in the sample gas. The compensation voltage is applied to the electrodes 506 and 606 along with the asymmetric RF voltage to compensate for the displacement of ions from a particular chemical species offsetting transverse displacement generated by the alternating asymmetric RF voltage. The compensation voltage reduces or substantially eliminates net transverse displacement of the ionized analytes of that chemical species, which enables those ionized analytes to pass between the electrodes 506 and 606. All other ions undergo a net displacement and are neutralized on contact with either electrode 506 or electrode 606.

It is noted that the electrical waveform generated by the SGSP 810 may operate at a maximum voltage for a selected RF field. As a maximum amplitude of the asymmetric RF voltage changes, the amplitude of the compensation voltage required for passage of ions of a particular chemical species between the outer electrode 506 and the inner electrode 606 also changes.

After passing between the outer electrode 506 and the inner electrode 606, the carrier gas then transports the remaining filtered ionized analytes along a flow path through the insulators 508 and 608 (see FIG. 8B, path 840) to the collector electrodes 510 and 610 (see FIG. 8B, path 842). The collector electrodes 510 and 610 are electrically coupled to electrical ground of the amplifier 406 by wires 818A-B. The wires 816A-B may be positioned within the non-conductive portion of the inner assembly 402 and the outer assembly 404. The amplifier 406 may measure the electrical current caused by the ionized analytes colliding with the collector electrodes 510 and 610 at a particular compensation voltage. The electrical current may be used to identify the presence or absence of a chemical species based on a comparison and matching with the electrical current response of known chemical species.

The SGSP 810 may automatically vary the compensation voltage over a compensation voltage range for a given electric field to produce a spectrum of ionized analytes in the sample gas identifying the intensity of the ionized analytes at a particular compensation voltage. The spectrum of ionized analytes also may identify the intensity of any dopants or other molecules in the carrier gas. Intensity may refer to the amount of electrical current measured at a particular compensation voltage, for example. The compensation voltage range may be a range of voltages from a positive voltage to a negative voltage, between two positive voltages, or between two negative voltages. The spectrum of ionized analytes may be referred to as a mobility scan, an ionogram, or an ion spectra.

Chemical species within the carrier gas are identified based upon correlation of the spectrum of the ionized analytes in the carrier gas with previously determined spectra for known chemical species. The spectrum of ionized analytes produces peaks based on an amount of electrical current detected at various compensations voltages. The spectrum of ionized analytes may be compared against stored spectra of known compounds and/or molecules for the vapor detector 100 based on the applied electric field to identify whether a match exists between the sample spectrum and any spectra of known chemical species. A match with a spectrum of a known chemical species may indicate that the sample gas includes the known chemical species.

Figure 9A:
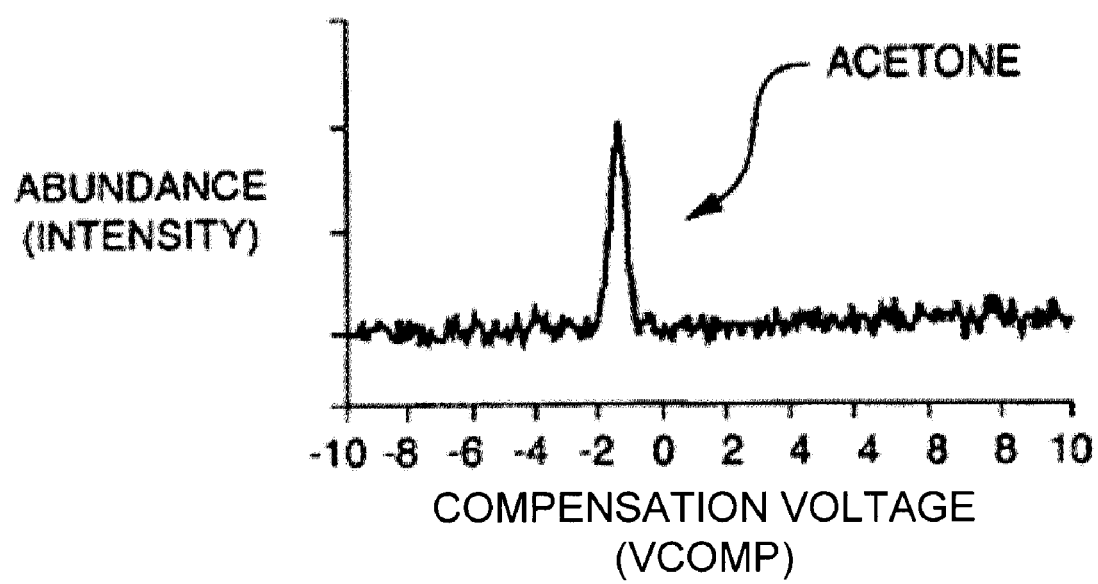
FIGS. 9A-B illustrates exemplary spectra of sample gas generated based on analyte analysis performed at an exemplary vapor detector.
Figure 9B:
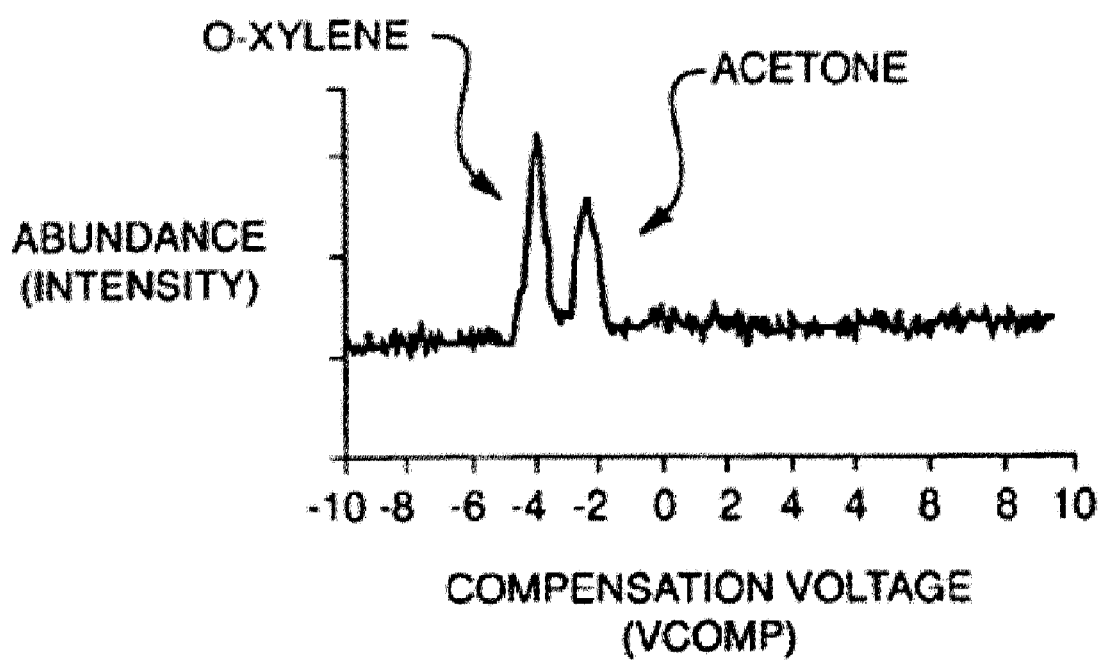

FIGS. 9A-9B illustrate an exemplary embodiment of a spectrum of ionized analytes in a carrier gas. FIG. 9A illustrates a spectrum generated based on acetone ions included in the carrier gas with the ion intensity being identified on the vertical axis (i.e., y axis), and the compensation voltage being identified on the horizontal axis (i.e., x axis). FIG. 9A illustrates detected acetone ions forming a peak intensity at a compensation voltage around −1.5 volts. Future detections of a peak at this compensation voltage may indicate detection of acetone in the sample gas. FIG. 9B illustrates a spectrum of ionized analytes generated based on acetone and an isomer of xylene (o-xylene) included in the carrier gas. As depicted, the acetone peak appears at a compensation voltage around −2.5 volts while the o-xylene peak appears at a compensation voltage around −4 volts.

The vapor detector 100 according to the various exemplary embodiments provides various advantages. For instance, the direction and circulation of the carrier gas flow through the vapor detector 100 provides various advantages. When contacting the membrane 802, the carrier gas flows in a direction on the second surface 806 opposite to the flow direction of the sample gas on the first surface 804 of the membrane 802. Having the counter flow is a more efficient means for picking up analytes permeating through the membrane 802 in the flow of the carrier gas. Also, the flow direction of the carrier gas permits the downstream addition of a restrictor/orifice after the membrane 802 for operating the analytical gap at a reduced pressure (if desired) while maintaining the membrane 802 at atmospheric pressure, as described, between the membrane 802 and the ionization source (e.g., ionization source 502 and/or 602).

The design of the carrier gas environment also may permit a compact design for the vapor detector 100. Compact design may permit use of the vapor detector 100 on site and may allow hand transport. For example, the vapor detector 100 may be physically transported to determine the presence of chemical warfare agent at a remote location. The vapor detector 100 integrates multiple components into a compact design for efficient transport of the vapor detector 100 to a remote location. The vapor detector 100 integrates the inlet assembly 104, the membrane 802, the ionization sources 502 and 602, the electrodes 506 and 606, the collector electrodes 510 and 610, and the amplifier 406 into a single unit, thereby facilitating transport of the vapor detector 100 to an on-site location.

The flow of the carrier gas at through the carrier inlet (see, e.g., flow path 828) and through the analytical gap (see, e.g., flow path 838) may be in opposite directions relative to one another, thus permitting compact placement of the carrier inlet 106 relative to the analytical gap between the inner assembly 402 and the outer assembly 404. This permits a compact cylindrical design for the vapor detector 100. Moreover, the radially spaced angled shafts 820 being radially offset from the series of radial shafts 846 may permit a compact design for transitioning the carrier gas from the carrier inlet 106 to the analytical gap (see e.g., flow paths 828, 830, 832, and 834).

The compact design of the vapor detector 100 also may provide for improved signal to noise ratios for more accurate identification of chemical species. The short length of the wires 818A-B between the collector electrodes 510 and 610 and the amplifier 406 advantageously reduces electrical signal noise and improves signal to noise ratio for the electrical current. The amplifier 406 receives a small electrical current from ionized analytes that collide with the collector electrodes 510 and 610, which act as a large impedance device. Placing the amplifier 406 near the collector electrodes 510 and 610 minimizes the amount of radiated and coupled electrical noise that may be picked up and passed into the amplifier 406, thus increasing the signal to noise ratio.

The vapor detector 100 also advantageously provides for increased resolution of the spectrum of the ionized analytes. A radial distance between the insulators 504 and 604 in a radial direction perpendicular to a longitudinal axis of the vapor detector 100 and/or a longitudinal width of the insulators 504 and 604 in a longitudinal direction may be varied to improve the resolution of the spectrum of the ionized analytes. The volume also may be modified to better identify chemicals of interest based on properties within a class of chemicals one desires to detect.

Generally, the volume of the ion reaction region 850 between the insulators 504 and 604 may be used to adjust the resolution of the spectrum. The vapor detector 100 may be adjustable to change the volume of space within of the ion reaction region 850, or multiple vapor detectors 100 may have ion reaction regions 850 of different volumes. Increasing or decreasing the volume of the ion reaction region 850 by either changing the radial or longitudinal distance, or both, may be used to optimize the resolution of the SGSP 810 by separating peaks in the spectrum of the ionized analytes that are near to one another. Increased resolution may limit the amount of overlap between the detected peaks and increase the ability to distinguish between two or more chemical species having a similar spectrum. The increased resolution may provide the vapor detector 100 with good sensitivity in order to provide the earliest possible alarms for the presence of hazardous vapors. Good sensitivity also provides a better chance of separating peaks at higher concentrations (i.e. better resolution of the vapor detector 100).

Increasing the volume of the ion reaction region 850 also increases the concentration of the ions passing between the electrodes 506 and 606. The increased concentration of ions also increases the probability that the spectrum includes one or more monomer peaks and reduces the likelihood of the occurrence of dimer peaks. A monomer is a molecule that may become chemically bonded to other monomers to form a polymer. Monomer peaks may be peaks in the spectrum representing a large intensity of monomer ions within a narrow compensating voltage range (see FIG. 9A). A dimer is a molecule composed of two similar subunits or monomers linked together. A dimer peak may occur over a broader compensation voltage range than a monomer peak and may spread over a compensation voltage range at the expense of monomer peaks. Dimer peaks may reduce the dynamic range and may saturate the vapor detector 100, thus inhibiting the vapor detector's ability to identify chemical species in the sample gas.

Figure 10:
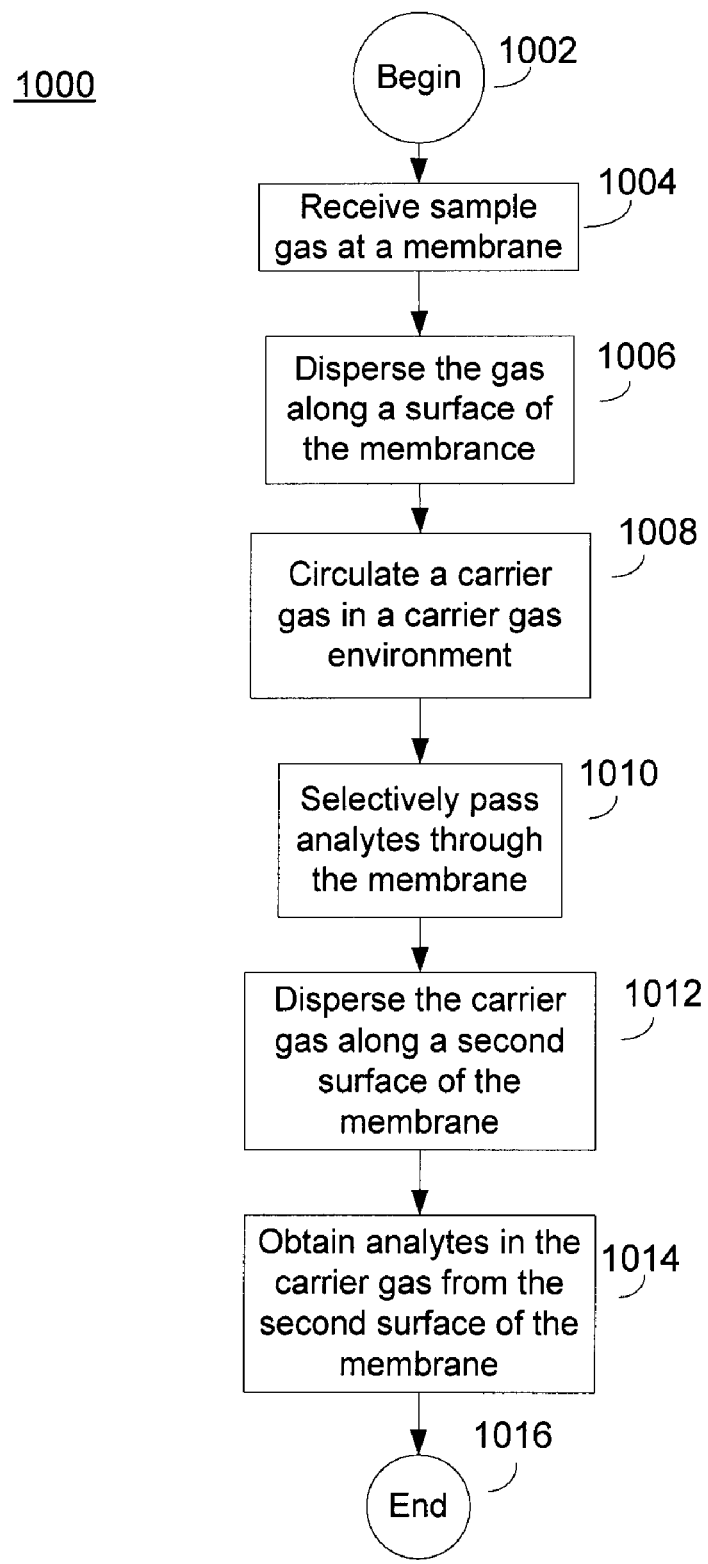
FIG. 10 illustrates an exemplary flow diagram for obtaining analytes of a sample gas from an ambient air environment to a carrier gas in a carrier gas environment of an exemplary vapor detector.

FIG. 10 illustrates a flow diagram of an exemplary method 1000 for obtaining analytes of a sample gas from an ambient air environment to a carrier gas in a carrier gas environment, according to an exemplary embodiment of the present invention. This exemplary method 1000 is provided by way of example, as there are a variety of ways to carry out methods according to the present disclosure. The method 1000 shown in FIG. 10 can be executed or otherwise performed by one or a combination of various systems. The method 1000 is described below as carried out by the vapor detector 100 shown in FIG. 1 by way of example, and various elements of the vapor detector 100 are referenced in explaining the example method of FIG. 10. Each block shown in FIG. 10 represents one or more processes, methods, and/or subroutines carried in the exemplary method. The method 1000 may begin at 1002 and may continue to 1004.

In 1004, an inlet assembly 104 of the vapor detector 100 receives a sample gas from an ambient environment due to a vacuum created by a sample pump 814. The inlet assembly 104 may minimize adherence of the chemicals within the sample gas to surfaces other than the first surface 804 of the membrane 802 through a diameter of the inlet 312 or including a heating element, for example.

In 1006, the inlet assembly 104 disperses the sample gas in substantially a first radial direction along the first surface 804 of the membrane 802 outward from the longitudinal axis of the vapor detector 100 toward an outer radius of the membrane 802.

In 1008, a gas distribution system 808 circulates the carrier gas through the carrier gas environment within the vapor detector 100.

In 1010, the membrane 802 selectively passes analytes of the sample gas therethrough from the first surface 804 to the second surface 806.

In 1012, the main assembly, which includes the inner assembly 402 and the outer assembly 404, directs the carrier gas through radially spaced angled shafts 820, which substantially disperse the carrier gas along the second surface 806 of the membrane 802 in a second radial direction from an outer radius of the second surface 806 toward the central longitudinal axis of the vapor detector 100.

In 1014, the carrier gas passes along and obtains the analytes from the second surface 806 of the membrane 802. The analytes in the carrier gas may then be carried through a central hole 812 to the series of radial shafts 846, which are offset from the angled shafts 820. The series of radial shafts 846 direct the analytes in the carrier gas to an analytical gap between the inner assembly 402 and the outer assembly 404 for chemical analysis. The method 1000 may continue to 1016 and end.

Figure 11:
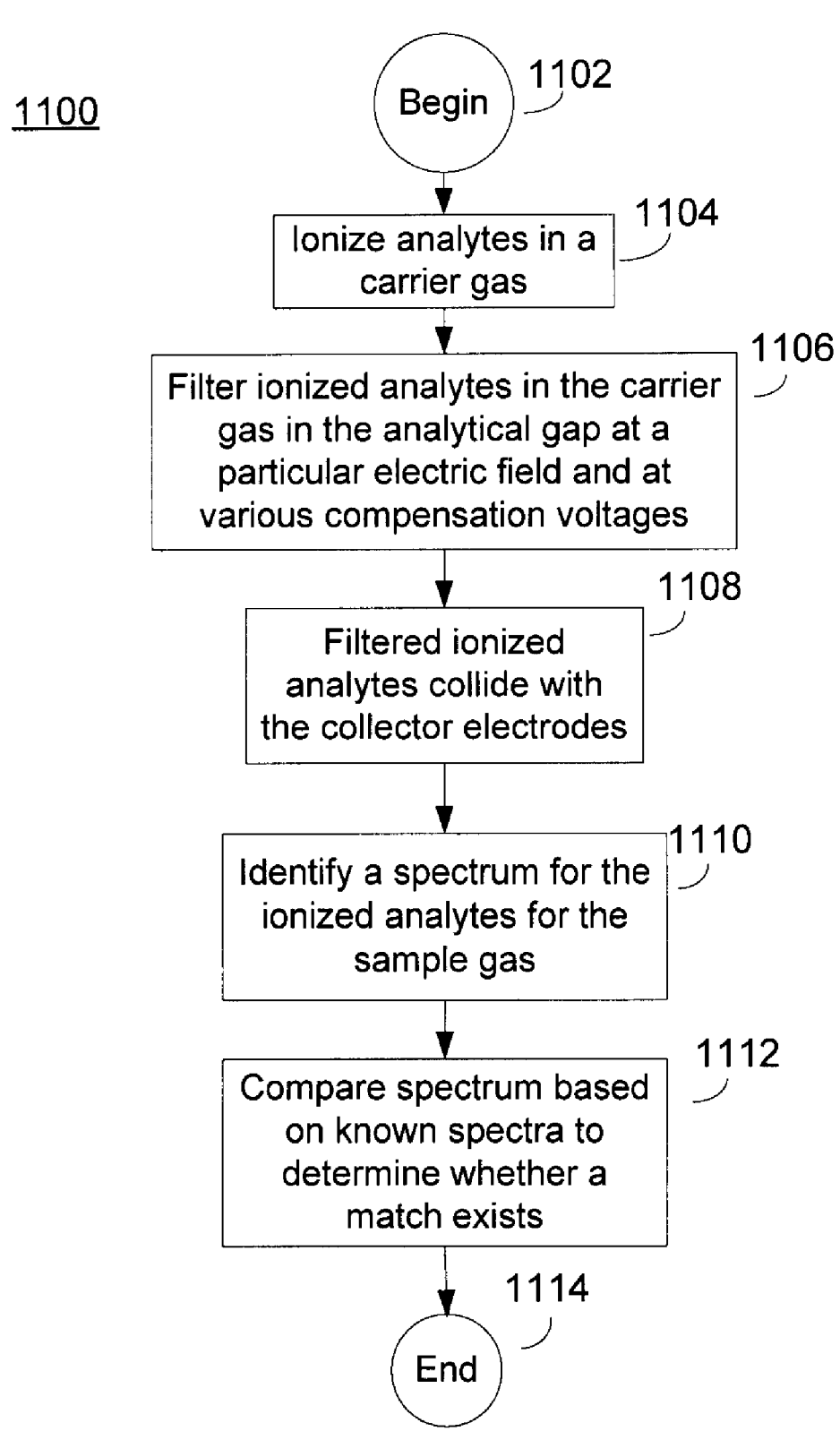
FIG. 11 illustrates an exemplary flow diagram for detecting chemical species based on analytes in a carrier gas using an exemplary vapor detector.

FIG. 11 illustrates a flow diagram of an exemplary method 1100 for detecting chemical species based on analytes in a carrier gas received in an analytical gap, according to an exemplary embodiment of the present invention. This exemplary method 1100 is provided by way of example, as there are a variety of ways to carry out methods according to the present disclosure. The method 1100 shown in FIG. 11 can be executed or otherwise performed by one or a combination of various systems. The method 1100 is described below as carried out by the vapor detector 100 shown in FIG. 1 by way of example, and various elements of the vapor detector 100 are referenced in explaining the example method of FIG. 11. Each block shown in FIG. 11 represents one or more processes, methods, and/or subroutines carried in the exemplary method. The method 1100 may begin at 1102 and may continue to 1104.

In 1104, the ionization sources 502 and 602 causes the analytes in the carrier gas circulating therebetween in the carrier gas environment to ionize in an ion reaction region 850.

In 1106, the SGSP 810 generates an electrical waveform placing an electric field along with various compensation voltages over a compensation voltage range between the electrodes 506 and 606 for filtering ionized analytes within the carrier gas. For a particular electric field, the SGSP 810 may generate various compensation voltages to filter the ionized analytes.

In 1108, the filtered ionized analytes are transported in the carrier gas and collide with the collector electrodes 510 and 610. The collision generates an electrical current by transferring the charge of the ionized analytes to the collector electrodes 510 and 610.

In 1110, the amplifier 406 amplifies the electrical current and the SGSP 810 may process the electrical current at the various compensation voltages in the compensation voltage range to identify a spectrum for the ionized analytes.

In 1112, the SGSP 810 compares the spectrum for the ionized analytes with various spectra for known chemical species and may determine whether a match exists. If a match exists, the SGSP 810 may output data indicating that the sample gas contains one or more chemical species based on the match with the known spectrum or spectra. If a match does not exist, the SGSP 810 may output data indicating that the sample gas does not match any known chemical species. The method 1100 may continue to 1114 and end.

It will be apparent to those skilled in the art that various modifications and variations can be made in the method of manufacture of the present invention and in construction and use of this vapor detector without departing from the scope or spirit of the invention. Other embodiments of the invention will be apparent to those skilled in the art from consideration of the specification and practice of the invention disclosed herein. It is intended that the specification be considered as exemplary only, with a true scope and spirit of the invention being indicated by the following claims.

Accordingly, while the present invention has been described here in detail in relation to its exemplary embodiments, it is to be understood that this disclosure is only illustrative and exemplary of the present invention and is made to provide an enabling disclosure of the invention. Accordingly, the foregoing disclosure is not intended to be construed or to limit the present invention or otherwise to exclude any other such embodiments, adaptations, variations, modifications and equivalent arrangements.

The invention claimed is:

1. An apparatus comprising:
a gas permeable selective isolation device including a first surface and a second surface;
an inlet assembly to receive sample gas from an ambient environment and to substantially disperse the sample gas along the first surface of the selective isolation device in a first radial direction; and
a main assembly defining a carrier gas environment for circulating a carrier gas, the main assembly comprising a carrier inlet to receive the carrier gas, the main assembly for substantially dispersing the carrier gas along the second surface of the selective isolation device in a second radial direction differing from the first direction, wherein the selective isolation device separates the ambient air environment from the carrier gas environment and selectively passes analytes in the sample gas therethrough; and the main assembly ionizing the analytes in the carrier gas.

2. The apparatus of claim 1, wherein the selective isolation device is a gas permeable membrane.

3. The apparatus of claim 1, wherein the main assembly further comprises:
   an inner ionization source; and
   an outer ionization source being radially spaced from the inner ionization source, the inner ionization source and the outer ionization source to ionize the analytes in the carrier gas for producing ionized analytes in an ion reaction region.

4. The apparatus of claim 3, wherein the main assembly further comprises:
   an inner electrode; and
   an outer electrode being radially spaced from the inner electrode, the inner electrode and the outer electrode to receive an electrical waveform producing an electric field therebetween to filter the ionized analytes for producing filtered ionized analytes.

5. The apparatus of claim 4, wherein the main assembly further comprises:
   an inner collector electrode; and
   an outer collector electrode being radially spaced from the inner collector electrode, the filtered ionized analytes contacting the inner collector electrode and/or the outer collector electrode to produce an electrical current.

6. An apparatus comprising:
   a gas permeable selective isolation device including a first surface and a second surface;
   an inlet assembly to receive sample gas from an ambient environment and to substantially disperse the sample gas along the first surface of the selective isolation device in a first radial direction; and
   a main assembly defining a carrier gas environment for circulating a carrier gas, the main assembly comprising a carrier inlet to receive the carrier gas, the main assembly for substantially dispersing the carrier gas along the second surface of the selective isolation device in a second radial direction differing from the first direction, wherein the selective isolation device separates the ambient air environment from the carrier gas environment and selectively passes analytes in the sample gas therethrough; and
   wherein the selective isolation device is an isolation valve.

7. An apparatus comprising:
   a gas permeable selective isolation device including a first surface and a second surface;
   an inlet assembly to receive sample gas from an ambient environment and to substantially disperse the sample gas along the first surface of the selective isolation device in a first radial direction; and
   a main assembly defining a carrier gas environment for circulating a carrier gas, the main assembly comprising a carrier inlet to receive the carrier gas, the main assembly for substantially dispersing the carrier gas along the second surface of the selective isolation device in a second radial direction differing from the first direction, wherein the selective isolation device separate the ambient air environment from the carrier gas environment and selectively passes analytes in the sample gas therethrough; and wherein the main assembly further comprises a plurality of radially spaced angled shafts coupled to the carrier inlet, the plurality of radially spaced angled shafts for directing the carrier gas to an outer radius of the second surface of the selective isolation device.

8. The apparatus of claim 7, wherein the main assembly defines an analytical gap and further comprises a plurality of radial shafts radially offset from the plurality of radially spaced angled shafts, the plurality of radial shafts for directing the carrier gas into the analytical gap.

9. An apparatus comprising:
   an inlet assembly comprising a gas permeable selective isolation device, the inlet assembly for receiving sample gas from an ambient environment and for substantially dispersing the sample gas along a first surface of the selective isolation device in a first direction; and
   a main assembly coupled to the inlet assembly and comprising a carrier inlet to receive a carrier gas, the main assembly defining a carrier gas environment and substantially dispersing the carrier gas along a second surface of the selective isolation device in a second direction, wherein the selective isolation device separates the ambient environment from the carrier gas environment and selectively passes analytes in the sample gas through the selective isolation device from the first surface to the second surface; and
   the main assembly ionizing the analytes in the carrier gas.

10. The apparatus of claim 9, wherein the main assembly further comprises:
    an inner ionization source; and
    an outer ionization source being radially spaced from the inner ionization source, the inner ionization source and the outer ionization source to ionize the analytes in the carrier gas for producing ionized analytes in an ion reaction region.

11. The apparatus of claim 10, wherein the main assembly further comprises:
    an inner electrode; and
    an outer electrode being radially spaced from the inner electrode, the inner electrode and the outer electrode to receive an electrical waveform producing an electric field therebetween to filter the ionized analytes for producing filtered ionized analytes.

12. The apparatus of claim 11, wherein the main assembly further comprises:
    an inner collector electrode; and
    an outer collector electrode being radially spaced from the inner collector electrode, the filtered ionized analytes contacting the inner collector electrode and/or the outer collector electrode to produce an electrical current.

13. An apparatus comprising:
    an inlet assembly comprising a gas permeable selective isolation device, the inlet assembly for receiving sample gas from an ambient environment and for substantially dispersing the sample gas along a first surface of the selective isolation device in a first direction; and
    a main assembly coupled to the inlet assembly and comprising a carrier inlet to receive a carrier gas, the main assembly defining a carrier gas environment and substantially dispersing the carrier gas along a second surface of the selective isolation device in a second direction, wherein the selective isolation device separates the ambient environment from the carrier gas environment and selectively passes analytes in the sample gas through the selective isolation device from the first surface to the second surface; and wherein the main assembly further comprises a plurality of radially spaced angled shafts coupled to the carrier inlet, the plurality of radially spaced angled shafts for directing the carrier gas to an outer radius of the selective isolation device.

14. The apparatus of claim 13, wherein the main assembly defines an analytical gap and further comprises a plurality of radial shafts radially offset from the plurality of radially spaced angled shafts, the plurality of radial shafts for directing the carrier gas into the analytical gap.

15. A system comprising:
a sampling pump for circulating a sample gas from an ambient environment;
a gas distribution system for circulating a carrier gas; and
a vapor detector coupled to the sampling pump and to the gas distribution system, the vapor detector comprising:
  a main assembly comprising a carrier inlet to receive the carrier gas from the gas distribution system, the main assembly defining a carrier gas environment for circulating the carrier gas; and
  an inlet assembly coupled to the main assembly and to the sampling pump, the inlet assembly comprising a gas permeable selective isolation device, the inlet assembly for receiving the sample gas from the ambient environment by a vacuum created by the sampling pump, the selective isolation device for separating the ambient environment from the carrier gas environment and for selectively passing analytes in the sample gas therethrough; and
the main assembly ionizing the analytes in the carrier gas.

16. The system of claim 15, wherein the main assembly further comprises:
an inner ionization source; and
an outer ionization source being radially spaced from the inner ionization source, the inner ionization source and the outer ionization source to ionize the analytes in the carrier gas and for producing ionized analytes in an ion reaction region.

17. The system of claim 16, wherein the main assembly further comprises:
an inner electrode; and
an outer electrode being radially spaced from the inner electrode, the inner electrode and the outer electrode to receive an electrical waveform producing an electric field therebetween to filter the ionized analytes to produce filtered ionized analytes.

18. The system of claim 17, wherein the main assembly further comprises:
an inner collector electrode; and
an outer collector electrode being radially spaced from the inner collector electrode, the filtered ionized analytes contacting the inner collector electrode and/or the outer collector electrode to produce an electrical current.

19. The system of claim 18, further comprising a signal generator coupled to the vapor detector for generating the electrical waveform.

20. The system of claim 19, further comprising a signal processor coupled to the vapor detector to identify a spectrum of the filtered ionized analytes based on the electric current and to determine whether a match exists between the spectrum with one or more spectra of known chemicals.

21. A system comprising:
a sampling pump for circulating a gas from an ambient environment;
gas distribution system for circulating a carrier gas; and
a vapor detector coupled to the sampling pump and to the distribution system, the vapor detector comprising:
  a main assembly comprising a carrier inlet to receive the carrier gas from the gas distribution system, the main assembly defining a carrier gas environment for circulating the carrier gas; and
  an inlet assembly coupled to the main assembly and to the sampling pump, the inlet assembly comprising a gas permeable selective isolation device, the inlet assembly for receiving the sample gas from the ambient environment by a vacuum created by the sampling pump, the selective isolation device for separating the ambient environment from the carrier gas environment and for selectively passing analytes in the sample gas therethrough; and
wherein the main assembly further comprises a plurality of radially spaced angled shafts coupled to the carrier inlet, the plurality of radially spaced angled shafts for directing the carrier gas to an outer radius of the selective isolation device.

22. The system of claim 21, wherein the main assembly further comprises a plurality of radial shafts radially offset from the plurality of radially spaced angled shafts, the plurality of radial shafts for directing the carrier gas into an analytical gap.

* * * * *